United States Patent [19]

Weis

[11] 4,282,358
[45] Aug. 4, 1981

[54] PROCESS FOR THE PRODUCTION OF SUBSTITUTED N-METHYLBENZOXAZINES

[75] Inventor: Claus D. Weis, Pfeffingen, Switzerland

[73] Assignee: Ciba-Geigy Corporation, Ardsley, N.Y.

[21] Appl. No.: 108,855

[22] Filed: Dec. 31, 1979

[30] Foreign Application Priority Data

Jan. 10, 1979 [CH] Switzerland ............. 216/79

[51] Int. Cl.³ ............... C07D 265/38; C07D 498/04
[52] U.S. Cl. .................................. 544/101; 544/102
[58] Field of Search ................................ 544/102, 101

[56] References Cited

U.S. PATENT DOCUMENTS

| | | | |
|---|---|---|---|
| 2,947,746 | 8/1960 | Olmsted | 544/102 |
| 3,215,692 | 11/1965 | Eros et al. | 544/102 |
| 3,506,658 | 4/1970 | Farge et al. | 544/102 |
| 3,629,477 | 12/1971 | Model et al. | 424/290 |
| 3,746,707 | 7/1973 | Gulbenk et al. | 544/101 |

OTHER PUBLICATIONS

J. P. Bourquin et al., Helv. Chim Acta, 41, 1061 (1958) and 42, 259 (1959).
Rodd's Chemistry of Carbon Compounds, vol. 4, New York 1978, p. 471ff.
H. Gilman and L. O. Moore, J. Chem. Soc. 79, 3485 (1957).

*Primary Examiner*—Henry R. Jiles
*Assistant Examiner*—Jane T. Fan
*Attorney, Agent, or Firm*—Edward McC. Roberts; John P. Spitals

[57] ABSTRACT

Substituted N-methylbenzoxazines of the formula

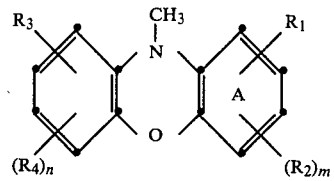

wherein the ring A can also contain a nitrogen atom as ring member, each of $R_1$ and $R_3$ independently is hydrogen, lower alkyl, halogen, nitro or trifluoromethyl, each of $R_2$ and $R_4$ independently is hydrogen or halogen and each of m and n is an integer from 1 to 3, are obtained by cyclizing compounds of the formula

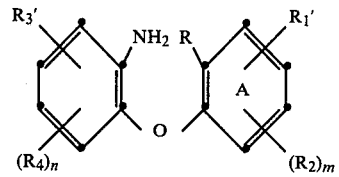

wherein A, $R_2$, $R_4$, m and n are as defined above, R is chlorine or bromine, and each of $R_1'$ and $R_3'$ independently is hydrogen, lower alkyl, halogen or trifluoromethyl, in the presence of dimethylmethanephosphonate, at reflux temperature, and, if desired, nitrating the resultant compounds.

5 Claims, No Drawings

PROCESS FOR THE PRODUCTION OF SUBSTITUTED N-METHYLBENZOXAZINES

The present invention relates to a process for the production of N-methylbenzoxazines.

It is known from J. P. Bourquin, G. Schwab, G. Gamboni, R. Fischer, L. Ruesch, S. Guldimann, V. Theus, E. Schenker and J. Renz, Helv. Chim. Acta, 41, 1061 (1958) and 42, 259 (1959), that a normal cyclisation between an amino group and a halogen atom in the 2- or 2'-position of a diphenyl ether, with attendant dehydrohalogenation, proceeds with poor yields.

This invention is based on the surprising observation that substituted N-methylbenzoxazines can be obtained in good yield by carrying out the cyclisation in the presence of a phosphonic acid derivative.

The process of the present invention for the production of substituted N-methylbenzoxazines of the formula

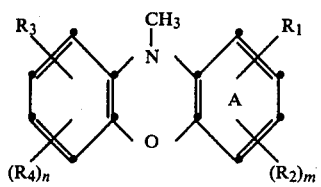
(I)

wherein the ring A can also contain a nitrogen atom as ring member, each of $R_1$ and $R_3$ independently is hydrogen, lower alkyl, halogen, nitro or trifluoromethyl, each of $R_2$ and $R_4$ independently is hydrogen or halogen and each of m and n is an integer from 1 to 3, comprises cyclising compounds of the formula

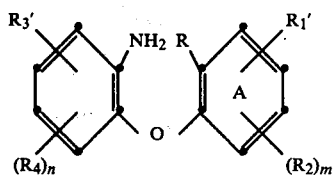
(2)

wherein A, $R_2$, $R_4$, m and n are as defined above, R is chlorine or bromine, and each of $R_1'$ and $R_3'$ independently is hydrogen, lower alkyl, halogen or trifluoromethyl, in the presence of dimethylmethanephosphonate, at reflux temperature, and, if desired, nitrating the resultant compounds.

Suitable lower alkyl radicals $R_1$ and $R_3$ are those containing 1 to 4 carbon atoms, preferably 1 carbon atom. Halogen is bromine and preferably chlorine.

Accordingly, by N-methylbenzoxazines are meant 10-methylphenoxazines and 10-methyl-1'-azaphenoxazines.

The process of the present invention is very suitable for the production of N-methylbenzoxazines of the formula

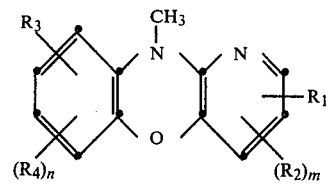
(3)

wherein each of $R_1$ and $R_3$ independently is hydrogen, lower alkyl, halogen, nitro or trifluoromethyl, each of $R_2$ and $R_4$ independently is hydrogen or halogen, and each of m and n is an integer from 1 to 3, by cyclisation of compounds of the formula

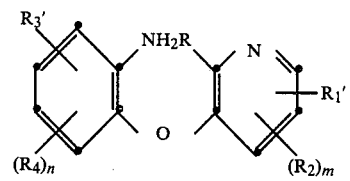
(4)

wherein R is chlorine or bromine, each of $R_1'$ and $R_3'$ independently is hydrogen, lower alkyl, halogen or trifluoromethyl, and $R_2$, $R_4$, m and n are as defined above, and, if desired, nitration of the resulting compounds; and also for the production of N-methylbenzoxazines of the formula

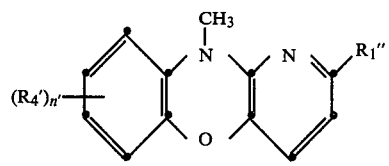
(5)

wherein $R_1''$ is halogen or methyl, $R_4'$ is halogen and n' is 1 or 2, by cyclisation of compounds of the formula

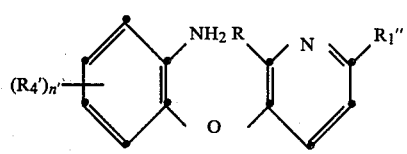
(6)

wherein $R_1''$, $R_4'$ and n are as defined above, and R is chlorine or bromine.

The process of the invention is especially suitable for the production of N-methylbenzoxazines of the formula

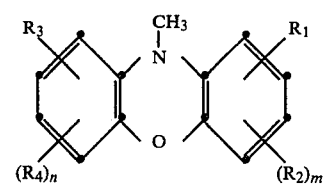
(7)

wherein each of $R_1$ and $R_3$ independently is hydrogen, lower alkyl, halogen, nitro or trifluoromethyl, each of $R_2$ and $R_4$ independently is hydrogen or halogen, and each of m and n is an integer from 1 to 3, by cyclisation of compounds of the formula

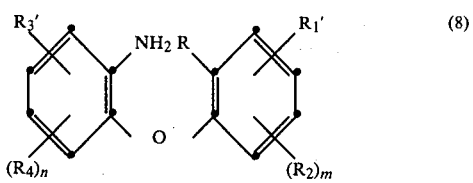

wherein R is chlorine or bromine and each of $R_1'$ and $R_3'$ independently is hydrogen, lower alkyl, halogen or trifluoromethyl, and $R_2$, $R_4$, m and n are as defined above, and, if desired, nitration of the resulting compounds; and, most particularly, for the production of N-methylbenzoxazines of the formula

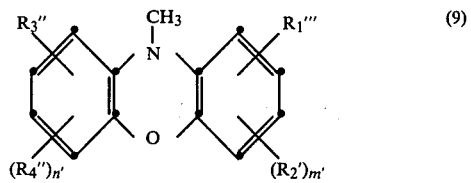

wherein $R_1'''$ is hydrogen, chlorine, bromine, methyl or trifluoromethyl, $R_3''$ is hydrogen, chlorine or bromine, and each of m' and n' independently is 1 or 2, by cyclisation of compounds of the formula

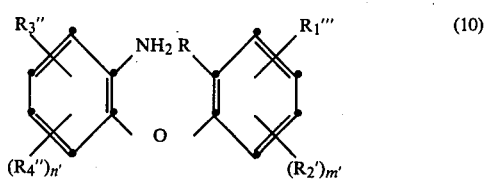

wherein $R_1'''$, $R_2'$, $R_3''$, $R_4''$, m' and n' are as defined above and R is chlorine or bromine.

Some of the starting materials of the formulae (2), (4), (6), (8) and (10) are known. The new starting materials can be prepared by methods which are known per se, e.g. by condensation of correspondingly substituted o-chloronitrobenzenes with correspondingly substituted halogenated phenols in the melt, in the temperature range between 100° and 160° C., preferably between 120° and 150° C., in the presence of potassium hydroxide (cf. for example U.S. Pat. No. 3,629,477). The isolated, correspondingly substituted 2-phenoxynitrobenzenes are then reduced in a manner known per se to the corresponding amine derivatives, e.g. by low pressure hydrogenation in the presence of Raney nickel and in an inert organic solvent, e.g. dioxane. In the preparation of starting materials (4) and (6), correspondingly substituted 3-hydroxypyridines are used instead of the halogenated phenols.

The process of the invention makes it possible to obtain, in simple manner, compounds of the formula (1) which it would otherwise only be possible to obtain by N-methylation in the presence of sodium amide, sodium hydride and methyl halide (cf. Rodd's Chemistry of Carbon Compounds, Vol. 4, New York 1978, page 471 ff., and H. Gilman and L. O. Moore, J. Chem. Soc. 79, 3485 (1957). Further, compared with the known methods, the process of the invention has the advantage that the reaction time is considerably reduced and that the compounds of the formula (1) are obtained in higher yield.

The novel substituted N-methylbenzoxazines can be used as dyes for man-made organic material, especially polyester, and the non-nitrated compounds can also be used as antioxidants. As dyes, they impart a brilliant yellow shade to the polyester substrates.

The following Examples illustrate the invention, but imply no restriction to what is described therein. Percentages are by weight.

EXAMPLE 1

(a) A solution of 288.5 g (1 mole) of 5-chloro-2-(2',4'-dichlorophenoxy)-aniline in 1000 ml of dimethylmethanephosphonate is heated to reflux temperature for 114 hours. After cooling to room temperature, the reaction mixture is added to 7500 ml of water which contains 230 ml of conc. aqueous ammonia, and the batch is stirred for 30 minutes. The precipitated crystalline product is collected by filtration, washed with water and dried at 50°–60° C. and 3039.75 kPa, affording 258 g of compound of the formula

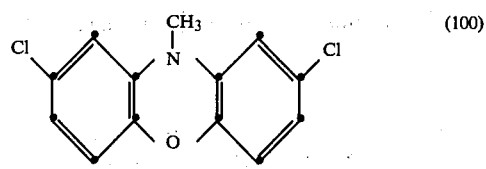

with a melting point of 96°–97.5° C. (after recrystallisation from petroleum ether).

The following compounds of the formula

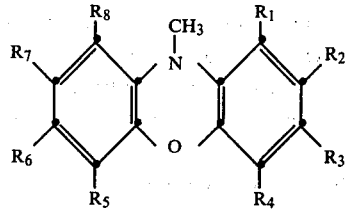

are obtained in analogous manner.

TABLE I

| Compound | $R_1$ | $R_2$ | $R_3$ | $R_4$ | $R_5$ | $R_6$ | $R_7$ | $R_8$ | m.p. °C. b.p. °C./kPa |
|---|---|---|---|---|---|---|---|---|---|
| 101 | $CH_3$ | | | | | | | | 142/70.9 |
| 102 | $CF_3$ | | | | | | | | 48.5–50 |
| 103 | Br | | | | | | Br | | 106–107 |
| 104 | Cl | | | | | Cl | | | 105.5–108 |
| 105 | | Cl | | | | Cl | | | 121–122 |
| 106 | Cl | Cl | | | | | Cl | | 154–156 |
| 107 | Cl | | | Cl | Cl | | | | 166.5–167 |
| 108 | Cl | Cl | | | Cl | Cl | | | 231–232 |

(b) The starting 5-chloro-2-(2',4'-dichlorophenoxy)-aniline is obtained as follows:

A reaction vessel is charged with 489 g (3 moles) of 2,5-dichlorophenol and 579 g (3 moles) of 2,4-dichloronitrobenzene and the mixture is heated, with stirring, to 120°–125° C. Then a solution of 200 g of solid potassium hydroxide (85%) in 130 ml of water is added in the course of 3 hours. The temperature is then raised to 140°–150° C. and kept thereat for 18 hours. The melt is cooled to 80°–100° C. and then added, with stirring, to a solution of 45 ml of 30% sodium hydroxide in 4500 ml of water. The crystalline precipitate is collected by filtration and dried. Recrystallisation from ethyl alcohol yields 803 g (84% of theory) of the compound of the formula

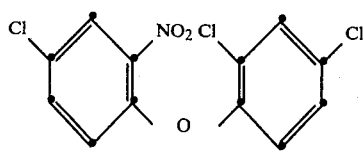
(200)

with a melting point of 84°–85° C. A solution of 497 g (1.5 moles) of this compound in 3000 ml of dioxane is hydrogenated in the presence of 50 g of Raney nickel for 8 hours at atmospheric pressure. Distillation of the oily product yields 394 g (91% of theory) of the compound of the formula

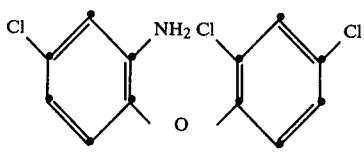
(201)

with a melting point of 67° C.

Repetition of the procedure described in (b) using correspondingly substituted phenols and nitrobenzenes yields the following compounds of the formula

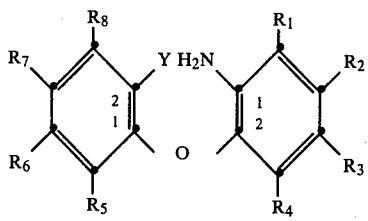

TABLE II

| Compound | Y | $R_1$ | $R_2$ | $R_3$ | $R_4$ | $R_5$ | $R_6$ | $R_7$ | $R_8$ | m.p. °C. b.p. °C./kPa |
|---|---|---|---|---|---|---|---|---|---|---|
| 202 | Br | $CH_3$ | | | | | | | | 159–163/101.3 |
| 203 | Br | $CF_3$ | | | | | | | | 111–113/0.4 |
| 204 | Br | Br | | | | | | Br | | 82–84 |
| 205 | Cl | Cl | | | | | | | Cl | 154–156/203.75 |
| 206 | Cl | | Cl | | Cl | | | | | 150–153/0.3 |
| 207 | Cl | Cl | Cl | | | | | | Cl | 88–91 |
| 208 | Cl | Cl | | | Cl | Cl | | | | 106–108 |
| 209 | Cl | Cl | Cl | | | Cl | Cl | | | 190–195/2.02 |

EXAMPLE 2

A suspension of 55.35 g (0.2 mole) of the compound of the formula

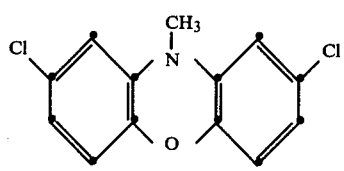
(300)

in 3000 ml of acetic acid is heated to 50° C. until homogenised. With stirring, 64.8 g (0.4 mole) of ferric chloride are added in the course of 15 minutes at 25° C., followed by the addition of 55.2 g (0.8 mole) of sodium nitrite. The reaction mixture is stirred at 50° C. for 20 hours. The crystalline precipitate is collected by suction filtration, washed with 500 ml of acetic acid and then dried, affording 71 g of the compound of the formula

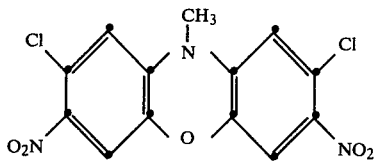
(301)

with a melting point of 302° C. (decomp.) after recrystallisation from nitrobenzene.

The compounds of the formula $R_8, R_7, R_6, R_5$ ... $CH_3$ ... $R_1, R_2, R_3, R_4$ are obtained in analogous manner.

TABLE III

| Compound | $R_1$ | $R_2$ | $R_3$ | $R_4$ | $R_5$ | $R_6$ | $R_7$ | $R_8$ | m.p. °C. |
|---|---|---|---|---|---|---|---|---|---|
| 302 | | Cl | | | | Cl | $NO_2$ | | 190.5–191.5 |
| 303 | | Cl | $NO_2$ | | | | Cl | | 248–250 |
| 304 | $NO_2$ | | Cl | | | Cl | | | 163.5–164.5 |
| 305 | | Cl | $NO_2$ | | Cl | Cl | | | 254–256 |

EXAMPLE 3

(a) A solution of 20 g (0.08 mole) of the compound of the formula

Cl—NH₂ Cl—N= (400)

in 100 ml of dimethylmethanephosphonate is heated to reflux in the course of 1 hour. After cooling, 600 ml of water are added to the reaction mixture, and the batch is stirred for 10 minutes. The precipitated crystalline product is collected by filtration, washed with water and dried at 60° C./202.65 kPa, affording 11.2 g (68.8% of theory) of the compound of the formula

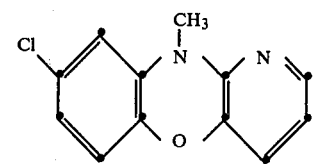
(401)

with a melting point of 103.5°–104.5° C. after recrystallisation from methyl alcohol.

Compounds of the formula

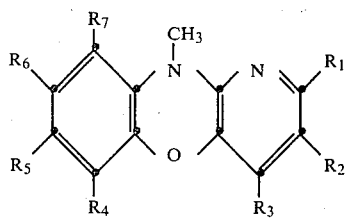

are obtained by repeating the above procedure using correspondingly substituted starting compounds.

TABLE IV

| Compound | $R_1$ | $R_2$ | $R_3$ | $R_4$ | $R_5$ | $R_6$ | $R_7$ | m.p. °C. |
|---|---|---|---|---|---|---|---|---|
| 402 | $CH_3$ | | | | | Cl | | 93.5–94.5 |
| 403 | $CH_3$ | | | | Cl | | | 118–119 |
| 404 | $CH_3$ | | | | Cl | Cl | | 143–144 |
| 405 | $CH_3$ | | | Cl | Cl | | | 187–188 |

(b) The starting 2-chloro-3-(2'-amino-4'-chlorophenoxy)-pyridine of the formula (400) is prepared as follows: With stirring, a mixture of 25.9 g (0.2 mole) of 2-chloro-3-hydroxypyridine and 38.4 g (0.2 mole) of 2,5-dichloronitrobenzene is heated to 120°–125° C. and to this mixture is added a solution of 13.17 g of solid 85% potassium hydroxide in 10 ml of water in the course of 2 hours. The hot suspension is mixed in a mixer with 300 ml of water. The crystalline precipitate is collected by filtration and washed with 1000 ml of water. A solution of 14.25 g (0.05 mole) of the resultant 2-chloro-3-(2-nitro-4-chlorophenoxy)-pyridine in 75 ml of dioxane is then hydrogenated in the presence of 15 g of Raney nickel. The catalyst is then removed by filtration, the filtrate is distilled and the precipitated crystalline product is collected by filtration and dried, affording 8.3 g of 2-chloro-3-(2'-amino-4'-chlorophenoxy)-pyridine of the formula (400) with a boiling point of 163°–167° C./50.76 kPa.

The compounds of the formula

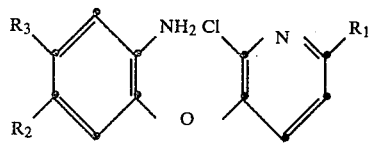

listed in Table V are obtained in analogous manner.

TABLE V

| Compound | $R_1$ | $R_2$ | $R_3$ | $R_4$ | m.p. °C. |
|---|---|---|---|---|---|
| 405 | $CH_3$ | Cl | | | 87–89 |
| 407 | $CH_3$ | | Cl | | 67–70 |
| 408 | $CH_3$ | Cl | Cl | | 137–139 |
| 409 | $CH_3$ | | Cl | Cl | 158.5–160 |

What is claimed is:

1. A process for the production of a N-methylbenzoxazine of the formula

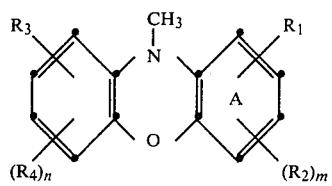

wherein the ring A can also contain a nitrogen atom as ring member, each of $R_1$ and $R_3$ independently is hydrogen, lower alkyl, halogen, nitro or trifluoromethyl, each of $R_2$ and $R_4$ independently is hydrogen or halogen, and each of m and n is an integer from 1 to 3, which process comprises cyclising a compound of the formula

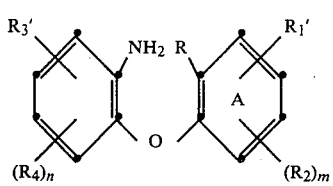

wherein A, $R_2$, $R_4$, m and n are as defined for formula (1), R is chlorine or bromine, and each of $R_1'$ and $R_3'$ independently is hydrogen, lower alkyl, halogen or trifluoromethyl, in the presence of dimethylmethanephosphonate, at reflux temperature, and, if desired, nitrating the resulting compound.

2. A process according to claim 1 for the production of a N-methylbenzoxazine of the formula

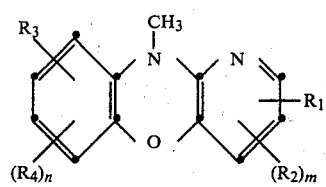

wherein each of $R_1$ and $R_3$ independently is hydrogen, lower alkyl, halogen, nitro or trifluoromethyl, each of $R_2$ and $R_4$ independently is hydrogen or halogen, and each of m and n is an integer from 1 to 3, which process comprises cyclising a compound of the formula

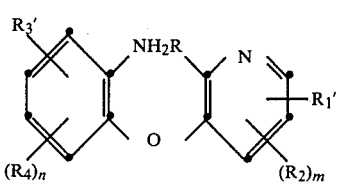

wherein R is chlorine or bromine, each of $R_1'$ and $R_3'$ independently is hydrogen, lower alkyl, halogen or trifluoromethyl, and $R_2$, $R_4$, m and n are as defined for formula (3), and, if desired, nitrating the resultant compound.

3. A process according to claim 2 for the production of a N-methylbenzoxazine of the formula

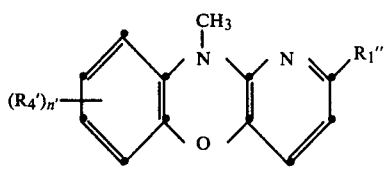

wherein $R_1''$ is halogen or methyl, $R_4'$ is halogen and $n'$ is 1 or 2, which process comprises cyclising a compound of the formula

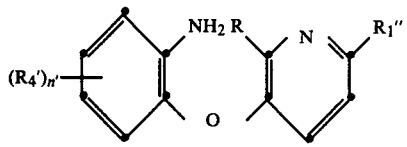

wherein $R_1''$, $R_4'$ and $n'$ are as defined for formula (5) and R is chlorine or bromine.

4. A process according to claim 1 for the production of a N-methylbenzoxazine of the formula

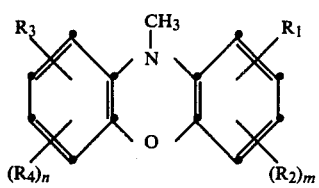

wherein each of $R_1$ and $R_3$ independently is hydrogen, lower alkyl, halogen, nitro or trifluoromethyl, each of $R_2$ and $R_4$ independently is hydrogen or halogen, and each of m and n is an integer from 1 to 3, which process comprises cyclising a compound of the formula

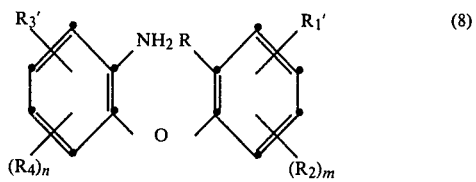

wherein R is chlorine or bromine and each of $R_1'$ and $R_3'$ independently is hydrogen, lower alkyl, halogen or trifluoromethyl, and $R_2$, $R_4$, m and n are as defined for formula (7), and, if desired, nitrating the resulting compound.

5. A process according to claim 4 for the production of a N-methylbenzoxazine of the formula

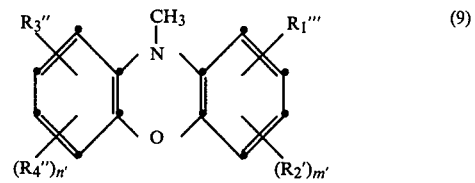

wherein $R_1'''$ is hydrogen, chlorine, bromine, methyl or trifluoromethyl, $R_3''$ is hydrogen, chlorine or bromine, each of $R_2'$ and $R_4''$ independently is hydrogen, chlorine or bromine, and each of $m'$ and $n'$ independently is 1 or 2, which process comprises cyclising a compound of the formula

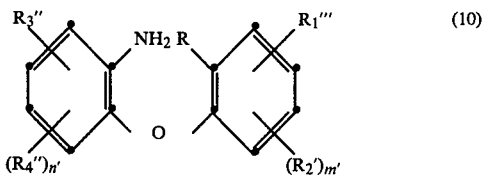

wherein $R_1'''$, $R_2'$, $R_3''$, $R_4''$, $m'$ and $n'$ are as defined for formula (9) and R is chlorine or bromine.

* * * * *